United States Patent [19]
Blumenfeld et al.

[11] Patent Number: 5,473,437
[45] Date of Patent: Dec. 5, 1995

[54] METHODS AND APPARATUS FOR DETECTING BACTERIAL GROWTH BY SPECTROPHOTOMETRIC SAMPLING OF A FIBER-OPTIC ARRAY

[75] Inventors: Walter Blumenfeld, Airville; Klaus W. Berndt, Stewartstown, both of Pa.

[73] Assignee: Becton Dickinson and Company, Franklin Lakes, N.J.

[21] Appl. No.: 420,885

[22] Filed: Apr. 11, 1995

Related U.S. Application Data

[63] Continuation of Ser. No. 245,714, May 18, 1994, abandoned, which is a continuation of Ser. No. 916,232, Jul. 17, 1992, abandoned.

[51] Int. Cl.[6] .......................... G01N 21/25; G01N 21/64; G01N 21/90; G01N 35/02
[52] U.S. Cl. .......................... 356/417; 435/34; 435/808; 436/47; 436/165; 436/172; 356/427
[58] Field of Search .......................... 356/39, 319, 427, 356/418, 417, 318; 250/328; 436/47, 165, 172; 435/291, 34, 39, 808, 173.1

[56] References Cited

U.S. PATENT DOCUMENTS

| | | | |
|---|---|---|---|
| 3,561,804 | 2/1971 | Brown | 292/67 |
| 3,697,185 | 10/1972 | Kassel et al. | 356/418 X |
| 3,946,239 | 3/1976 | Salzman et al. | 356/39 X |
| 4,152,213 | 5/1979 | Ahnell | 195/103.5 M |
| 4,456,380 | 6/1984 | Kondo et al. | 356/418 |
| 4,540,549 | 9/1985 | Manabe | 435/808 X |
| 4,685,801 | 8/1987 | Minekane | 436/47 X |
| 5,005,981 | 4/1991 | Schulte et al. | 366/219 |
| 5,112,134 | 5/1992 | Chow et al. | 356/427 |
| 5,210,590 | 5/1993 | Landa et al. | 356/319 |

FOREIGN PATENT DOCUMENTS

| 90/13663 | 11/1990 | WIPO. |
|---|---|---|
| WO92/08986 | 5/1992 | WIPO. |

Primary Examiner—Robert J. Warden
Assistant Examiner—E. Leigh Dawson
Attorney, Agent, or Firm—Alan W. Fiedler

[57] ABSTRACT

The detection of bacterial growth or the performance of other interrogative processes in multiple sample vials is accomplished using a moving rack that selectively couples optical locations to an optical excitation and detection system. The apparatus includes a drive mechanism combining agitation of the culture vials with a sequential scanning of an array of optical fibers, preferably by a spectrophotometric excitation and detection system. Selection of each culture vial provides, for example, optical detection of bacterial growth by fluorescence or other spectrophotometric measurements. A rack for holding vials is preferably the only moving assembly, and requires no mechanical or electrical interconnection with the excitation and detection system for its operation. In general, the present invention relates to the optically indexed presentation of the optical guides, to many remote sample sites in the form of a geometric array at the interface between the moving culture vial rack assembly and the spectrophotometric excitation and detection system fixed to the body of the instrument. Methods of transmitting and receiving electromagnetic radiation to and from sample vials held in a movable rack include the steps of coupling the sample vials to an optical fiber and terminating the optical fiber at an optical coupling location. The rack is then moved to align at least one of the coupling locations with an excitation and detection system.

16 Claims, 12 Drawing Sheets

METHODS AND APPARATUS FOR DETECTING BACTERIAL GROWTH BY SPECTROPHOTOMETRIC SAMPLING OF A FIBER-OPTIC ARRAY

This application is a continuation of application Ser. No. 08/245,714, filed May 18, 1994, now abandoned, which is a continuation of application Ser. No. 07/916,232, filed Jul. 17, 1992, now abandoned.

The present invention relates to non-invasive methods and apparatus for detecting biological activity in a specimen sample such as blood, that may include a culture medium and which is introduced into a sealable container or vial and exposed to conditions enabling metabolic processes to take place in the presence of any microorganisms in the sample.

BACKGROUND OF THE INVENTION

Usually, the presence of bacteria in a patient's body fluid, especially blood, is determined using blood culture vials. A small quantity of blood is injected through an enclosing rubber septum into a sterile sample vial containing a culture medium. The vial is incubated at normal human body temperature and monitored for bacterial growth. Common visual inspection involves monitoring the turbidity of the liquid suspension. Known instrumental methods detect changes in the $CO_2$ content of the culture vials, which is a metabolic by-product of the bacterial growth. Monitoring the $CO_2$ content can be accomplished by methods well established in the art, such as radiochemical, infrared absorption at a spectral line characteristic of $CO_2$, or pressure/vacuum measurement techniques such as those disclosed in Ahnell U.S. Pat. No. 4,152,213.

Recently, non-invasive methods have been developed involving the optical interrogation of chemical sensors disposed inside a sample vial that utilize colorimetric or fluorometric spectroscopic techniques. Some of these methods have also implemented remote sensing of multiple sample sites via optical fibers and switches. Additional non-invasive optical methods have been devised which rely on properties inherent in the liquid suspension and do not require the use of a chemical sensor; these include automated techniques for scattered photon migration measurements.

Typically, when using these non-invasive techniques, the sample vial must be agitated. Since it is both cost effective and time efficient to process samples in a batch, equipment must therefore be provided that agitates a large number of vials. Agitation, however, requires that the structure holding the vials moves relative to a stationary reference frame, and it is usually preferable to mount electronics and other equipment within the stationary portion of the system, not on the moving portion. This results in systems where both electrical cables and/or optical fibers must be designed to permit this relative motion by allowing sufficient excess at an appropriate point in the system. There remains a need, however, to permit a plurality of sample vials to be agitated while also permitting the interrogation of each vial by an optical fiber. It is accordingly an object of the present invention to provide an agitating rack and an optical excitation/detection system for transmitting electromagnetic energy to each sample vial in the rack and for receiving electromagnetic energy from each sample.

SUMMARY OF THE INVENTION

To fulfill this and other objects of the present invention, an instrument is provided for incubating and detecting bacterial growth in multiple sample vials. A drive mechanism is connected to a rack that combines agitation of the vials with the sequential coupling of one or more optical fibers to a spectrophotometric detector or similar sensor. Selection of each vial provides an optical signal useful in the detection of bacterial growth by fluorescence or other spectrophotometric measurements. The rack is preferably the only moving assembly, and requires no mechanical or electrical connection to an optical excitation/detection system for its operation. The present invention therefore eliminates the above-described flexing of electrical cables or optical fibers.

Thus, in a most preferred embodiment, the present invention provides apparatus for transmitting electromagnetic radiation to a plurality of sample vials and for receiving electromagnetic radiation from the sample vials. The apparatus includes a rack for retaining the plurality of sample vials and one or more optical guides coupled to each of the plurality of sample vials and to the rack at one or more optical coupling locations. An excitation/detection system is provided for transmitting and receiving electromagnetic radiation between the excitation/detection system and the sample vials using the optical guides that are aligned with the optical coupling locations.

The optical guide can include either a single optical fiber that terminates at a single optical coupling location, or multiple fibers that are grouped together to define an optical coupling location. Alternatively, the optical guide can include separate fibers for excitation and emission that transmit electromagnetic radiation to the sample vial and collect it from the sample vials, respectively. The fibers or groups of fibers can either be aligned with the central axis of the rack or arranged in one or more groups along a portion of the rack. In the embodiments using groups of either excitation fibers, emission fibers, or both, different types of systems are useful to enable electromagnetic energy to be transmitted to and collected from each individual sample vial.

Methods of transmitting electromagnetic radiation to sample vials and receiving electromagnetic radiation from the sample vials are also disclosed. In general, the present invention discloses the optically indexed presentation of the optical guides, e.g., the emission and excitation fibers, to many remote sample sites in the form of a geometric array at the interface between the moving culture vial rack assembly and the spectrophotometric excitation/detection system fixed to the body of the instrument. This interface is defined as an optical coupling location.

The methods of the present invention include the steps of coupling the sample vials to an optical fiber and terminating the optical fiber at an optical coupling location. The rack is then moved while aligning at least one of the optical coupling locations with the excitation/detection system.

BRIEF DESCRIPTION OF THE DRAWINGS

The various features, objects, benefits, and advantages of the present invention will become more apparent upon reading the following detailed description of the preferred embodiments, along with the appended claims in conjunction with the drawings, wherein like reference numerals identify corresponding components, and:

DETAILED DESCRIPTION OF THE PREFERRED EMBODIMENTS

Figure 1A:
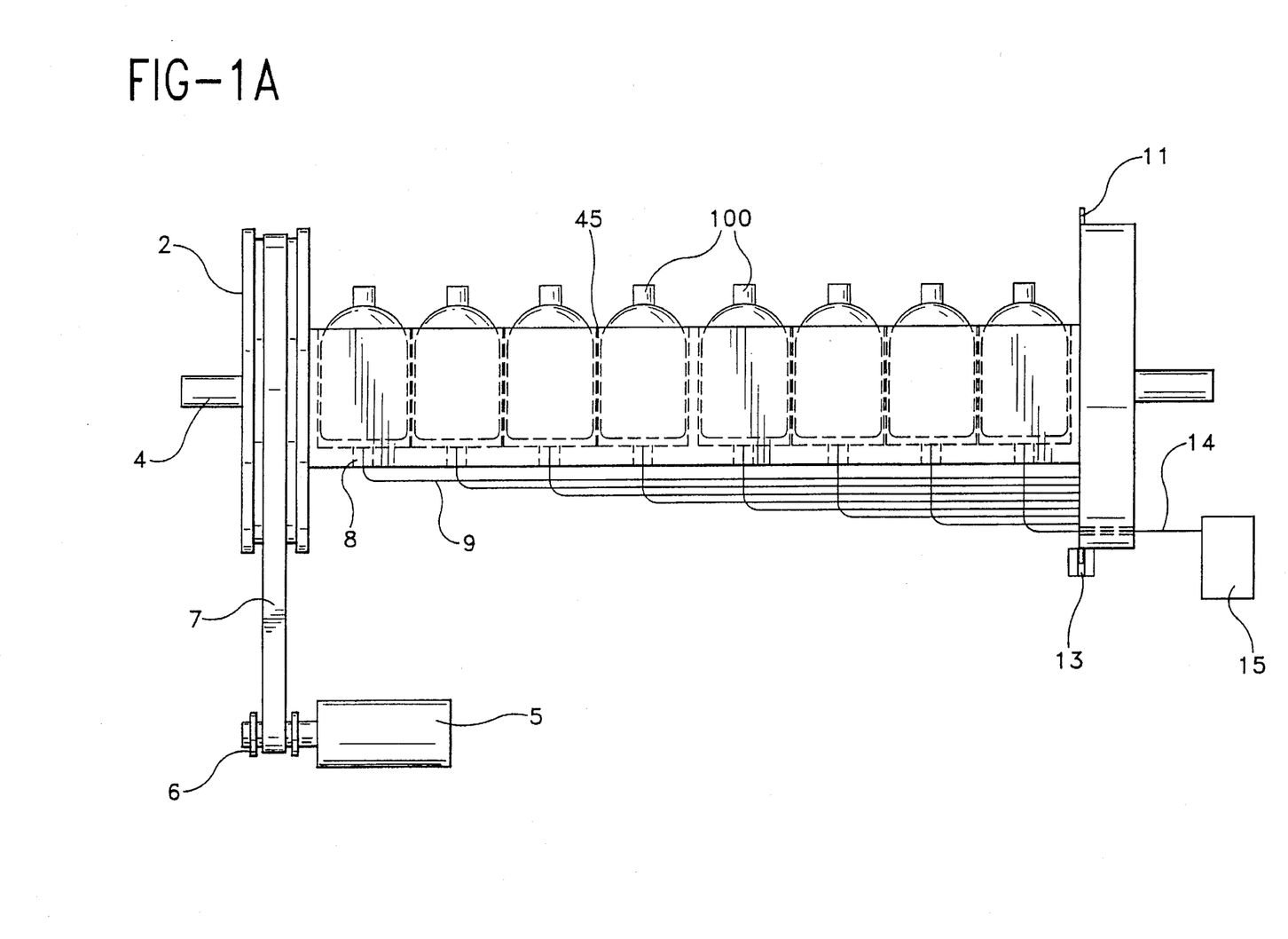
FIGS. 1A–1C respectively depict front elevation, plan, and side elevation views of a first embodiment of the rack apparatus of the present invention.

The various embodiments of the apparatus of the present invention are illustrated in FIGS. 1A–10B, with the apparatus generally designated as 1. A first embodiment of the apparatus of the present invention is depicted in FIGS. 1A–1C. A plurality of samples, each contained in an individual vial or container 100 are disposed in a rack 1. In this embodiment, the rack 1 is a block in which many cylindrical cavities have been bored, each sized to hold a single vial 100. A first end of the rack 1 is attached to a large drive pulley 2; a second end is attached to a circular sampling disk 3. The rack assembly 45 is supported by and rotates about an axis defined by a pivot shaft 4. The culture vials 100 held in the cavities of the rack 1 are preferably rocked or rotated by a stepper motor 5 that is connected to a small pulley 6. A belt 7 interconnecting the pulleys 2,6 to the stepper motor 5 controls the angular position of the rack 1.

Figure 1B:
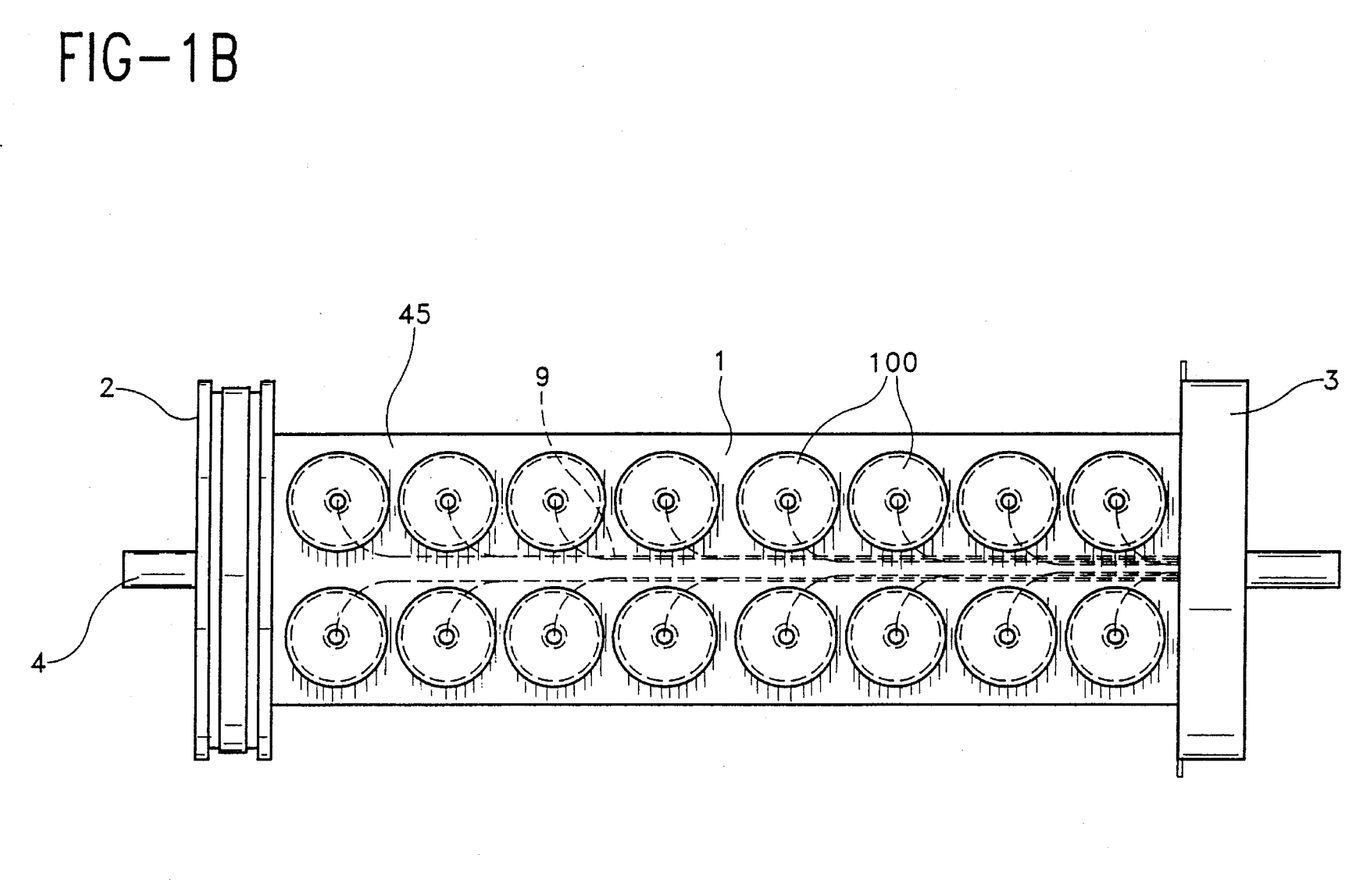
Figure 1C:
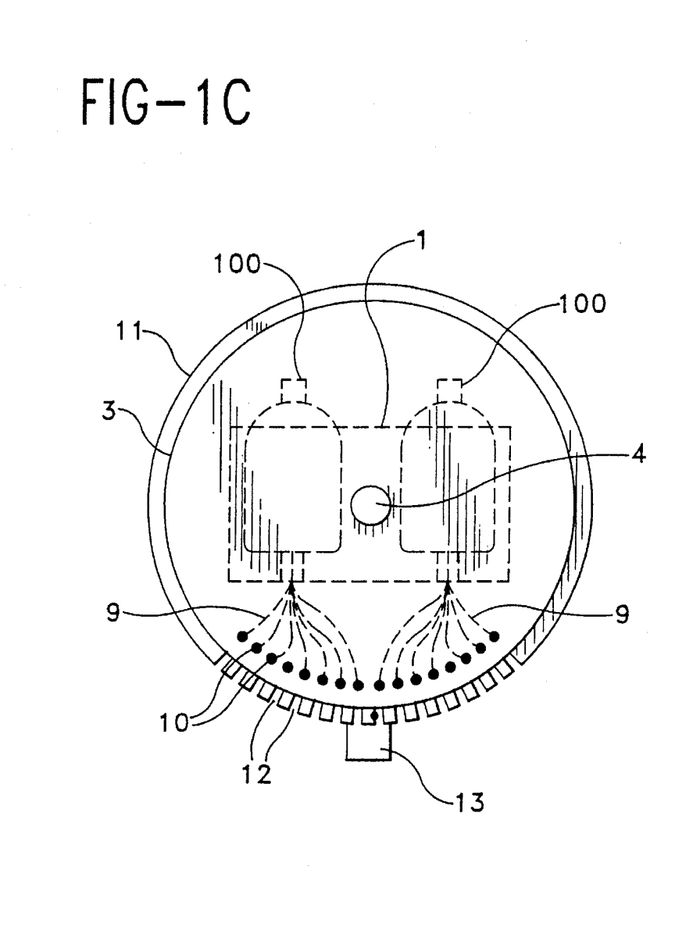

Those of skill in the art will understand that structural elements such as the pivot shaft bearings, mounts and supports required to locate the pivot shaft within the body of an instrument, and other associated structures, have been omitted from FIGS. 1A–1C and the other figures herein for clarity of description, as have the mechanical and electrical arrangements required to maintain the apparatus of the present invention at a constant temperature suitable to support the growth of any bacteria present within the culture vials in certain applications. Additionally, it should be noted at the outset numerous other drive systems such as, for one example, a gear train would be equivalent to and easily substituted for the belt 7 and pulleys 2,6 shown in FIGS. 1A–1C.

Referring still to FIGS. 1A–1C, in the bottom of each cavity is a through-hole 8, in which an optical fiber 9 is inserted and retained. The optical fibers 9 from each of the plurality of cavities terminate in an array of fiber ends 10 that extend through the sampling disk 3, with their centers preferably equally spaced along an arc centered on the axis of the pivot shaft 4, as shown in FIG. 1C. The angular increment between the centers of the fiber ends 10 most preferably corresponds to an integral number of steps of the stepper motor 5. A preferred manner for indexing the disclosed apparatus comprises providing a thin extended rim 11 on the perimeter of the sampling disk 3 in which a series of rectangular notches 12 has been cut. The leading edge of each notch is angularly aligned with the centerline of the nearest optical fiber end 10. As seen in FIG. 1A and illustrated in greater detail in FIG. 2, a transmissive optical index fiducial 13 is angularly aligned with the optical axis 14 of an excitation/detection system 15. In this way, the edge transition of a notch 12 through the fiducial 13 produces an electrical signal indicating the precise alignment of the excitation/detection system 15 with one of the optical fibers 9. When aligned, fluorescence from the vial 100 in the cavity which is also associated with that particular the optical fiber 9 is measured. In this embodiment the optical fiber 9 thus acts as both an excitation fiber by transmitting the energy received from the excitation/detection system to the vial 100, and as an emission fiber by receiving energy that escapes the vial 100 and transmitting it to the detection system.

Figure 2:
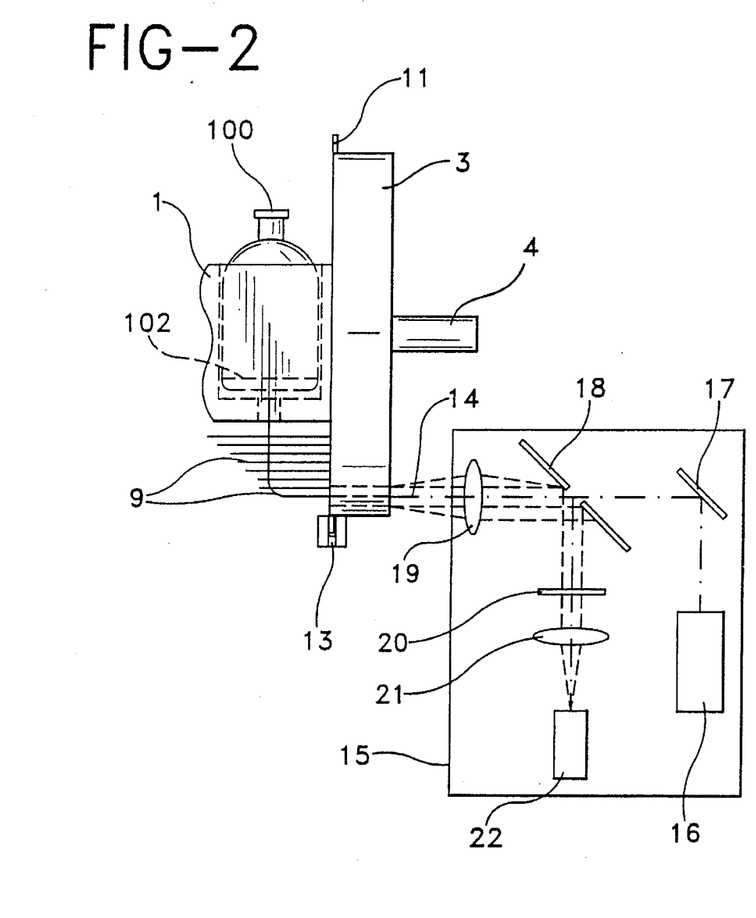
FIG. 2 is an enlarged partially schematic, partially broken away side elevation view depicting further details of the optical excitation/detection system used with the rack apparatus illustrated in FIGS. 1A–1C.

Additional details of the apparatus shown in FIGS. 1A–1C are illustrated in FIG. 2. A preferred embodiment of a fluorescence excitation/detection system 15 for use in the present invention is shown schematically. As explained above, the metabolic production of $CO_2$ by bacteria growing in the vial 100 can be determined by the fluorescence intensity of a chemical sensor 102 in the vial 100. Those of ordinary skill will understand that the sensor 102 may be a membrane or thin film disposed within the vial 100. As seen in FIG. 2, this fluorescence is preferably excited by a beam of electromagnetic radiation from a green Helium-Neon (He-Ne) laser 16 which is deflected by an alignment mirror 17 and passes through a small center hole in an emission mirror 18 and the center of the objective lens 19. The excitation beam travels along the optical axis 14 shown and is directed through the optical fiber 9, in its excitation mode, to interrogate the sensor 102 that is disposed in the bottom of the vial 100. Fluorescent emission is collected from the sensor 102 by the same optical fiber 9, now in its emission mode, and is acquired by the objective lens 19, but is deflected by the emission mirror 18 to an emission filter 20 and focused by a detector lens 21 on the photocathode of a photomultiplier tube 22. In other embodiments, the photomultiplier 22 can be a photodiode or other suitable detector. As is well known, the photomultiplier anode current is a measurement of the fluorescent emission intensity. As understood by those of ordinary skill, after correction for excitation intensity, as measured by an optical source monitor or laser current monitor (not shown), this intensity value serves as an indicator of bacterial growth in the culture medium.

The pierced mirror beam splitter and fiber-optic sampling of culture vial fluorescence shown in FIG. 2 uses conventional laser excitation technology as is the common practice in fluorescence measurement. The present invention is differentiated from other bacterial growth-based detection instruments, as discussed above, by the non-mechanical link from the rack 1 to the excitation/detection system 15, and by use of the agitation drive system to multiplex the measurement of a plurality of culture vials 100 via the array of optical fibers 9 optically connected to each of the vials and to the rack at a plurality of "optical coupling locations" that are in this case defined by the optical fiber ends 10. The present invention therefore provides an optically indexed presentation of the fiber-optic links 9 to many remote sample sites, i.e., each vial 100, in the form of a geometric array of optical coupling locations defined at the interface between the moving rack assembly 45 and the excitation/detection system 15, the latter being fixed relative to the body of the instrument. In operation, the rack 1 may either be "stepped" to stop at each optical coupling location or it may "sweep" smoothly through an arc, successively passing the optical coupling locations through the optical axis 14 of the beam.

Figure 3A:
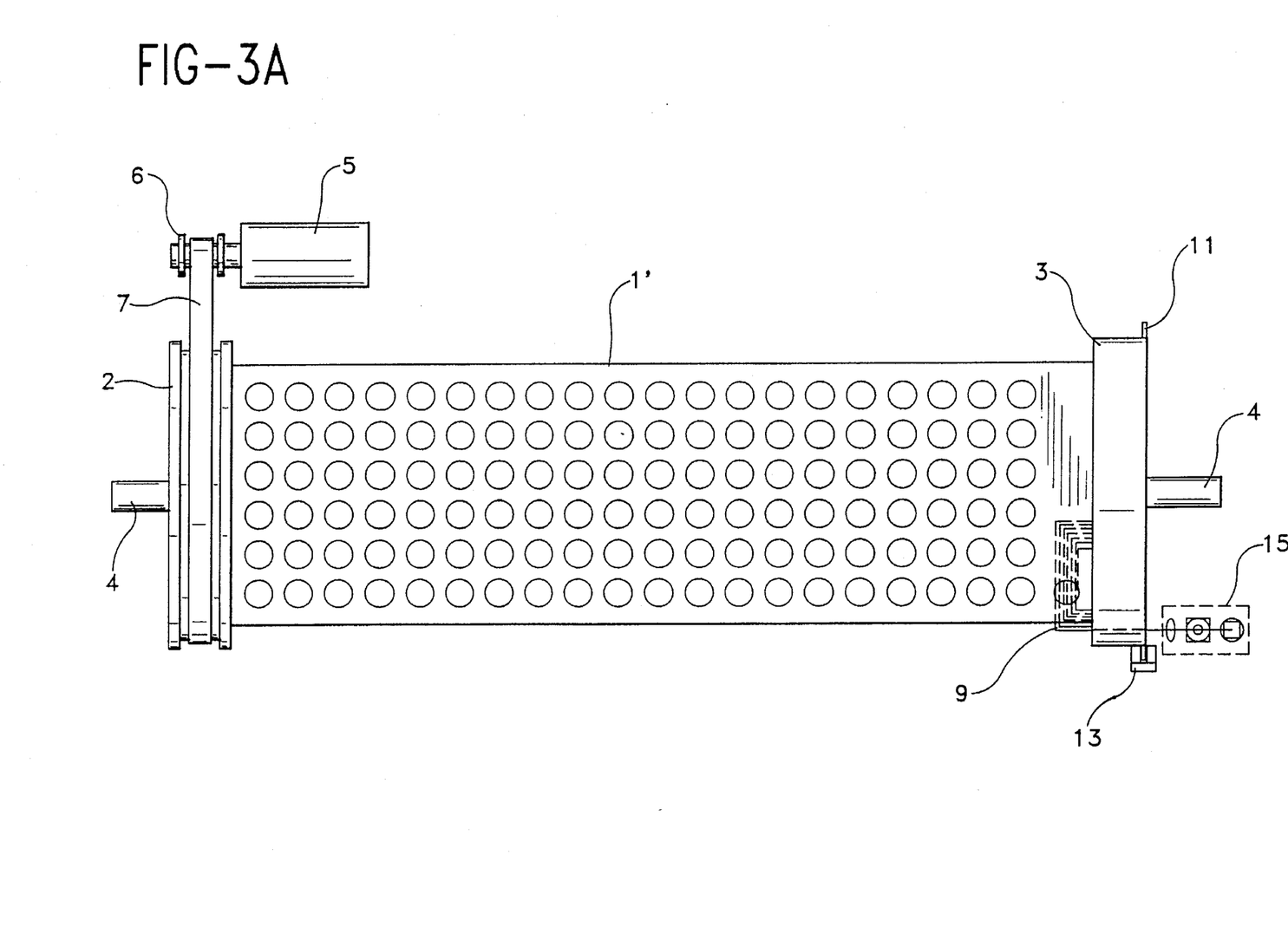
FIGS. 3A–3B show another embodiment of the apparatus of the present invention adapted to process 120 samples.
Figure 3B:
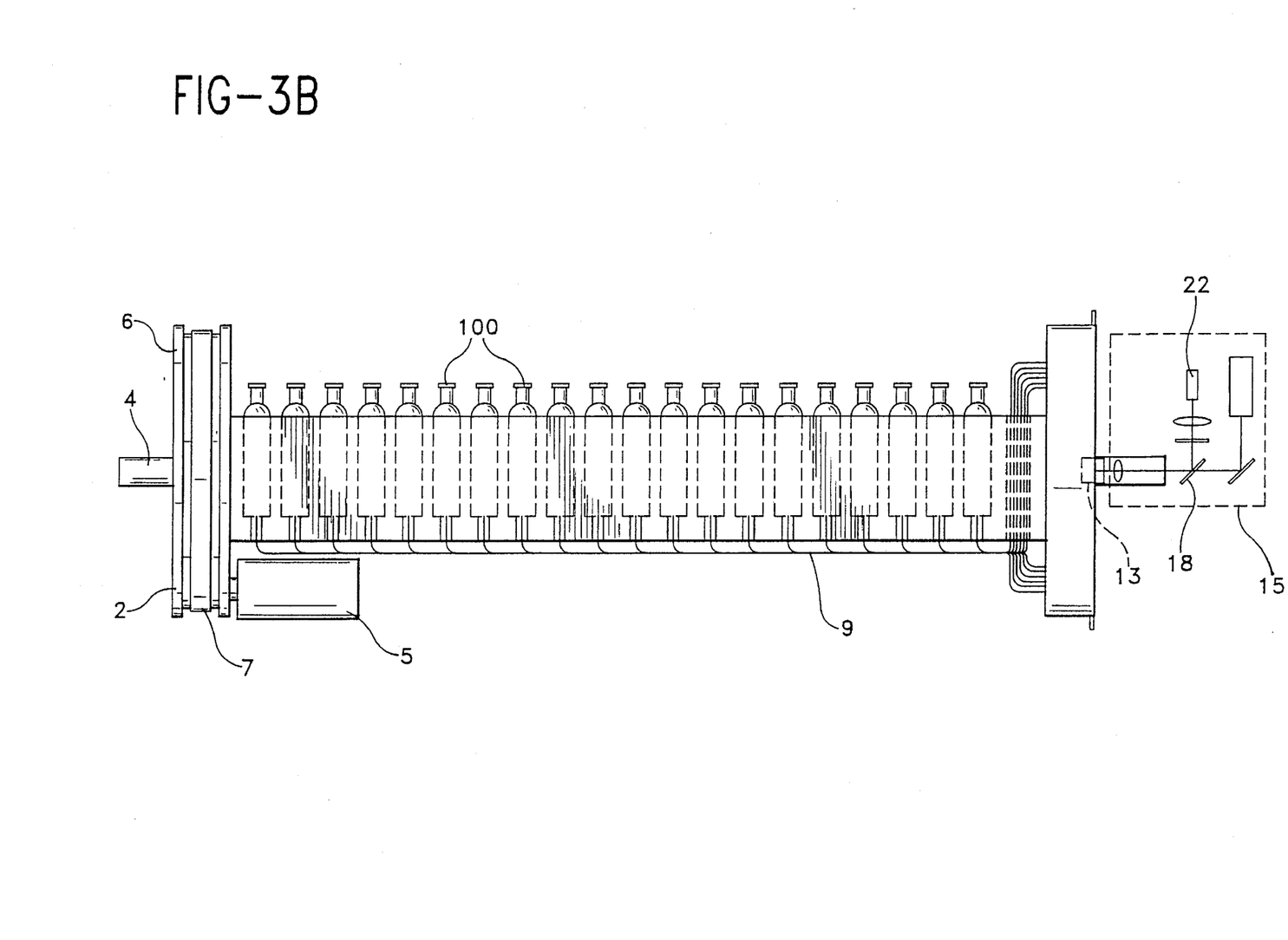

Another embodiment of the present invention on a scale suitable for a commercial instrument is shown in FIGS. 3A–3B. This embodiment of the present invention holds up to 120 culture vials 100, most preferably arranged in the rack 1' in an array of six rows and twenty columns, as shown in FIG. 3A. All components serve the same function as those described above with reference to FIGS. 1A–1C and 2, and are thus labeled with the same reference numerals. As will be understood by those of ordinary skill, apparatus made in accordance with the present invention can be constructed to accommodate any number of vials 100 by varying the number of rows and columns in the rack.

Figure 4:
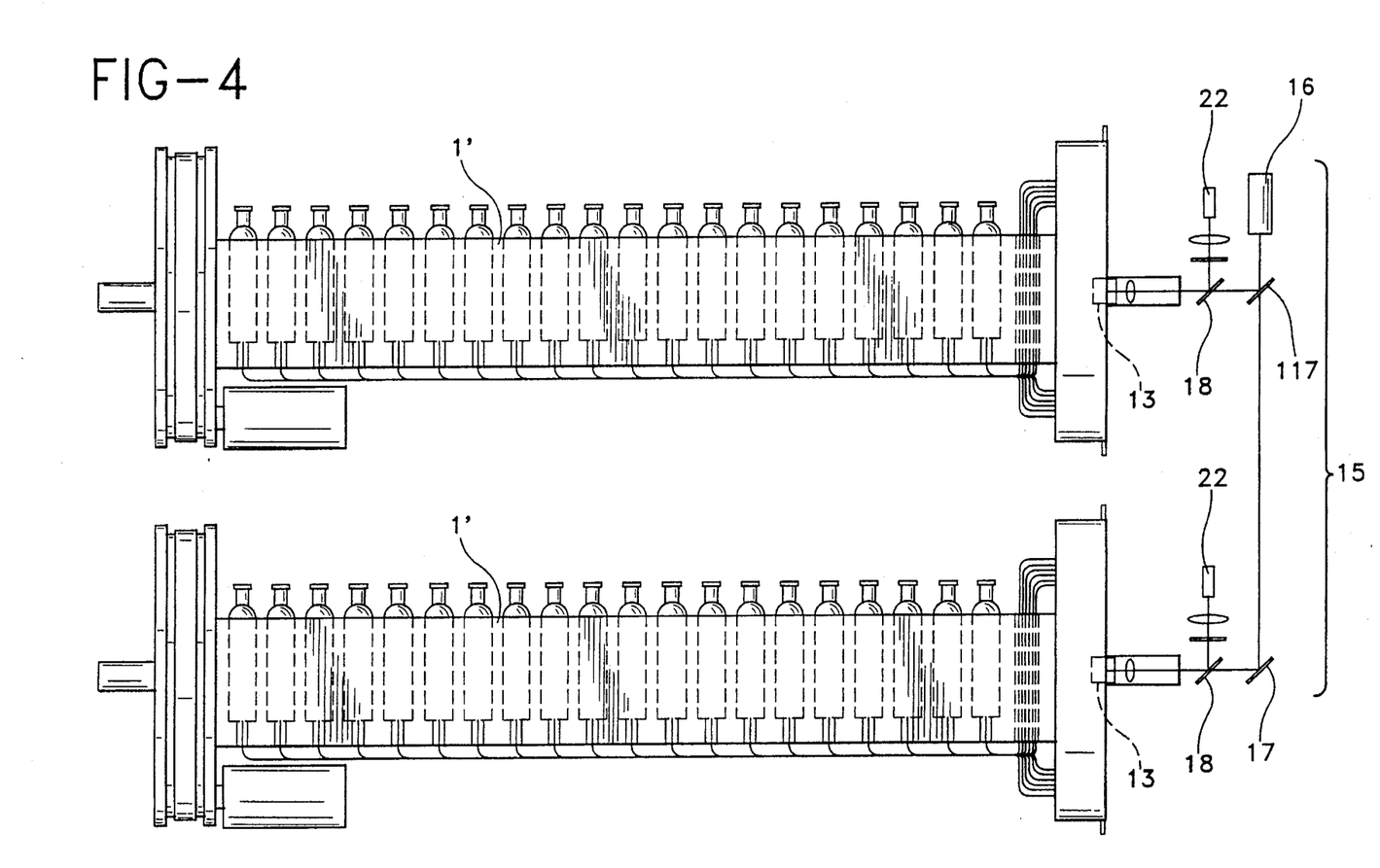
FIG. 4 is a partially schematic illustration of two of the apparatus depicted in FIGS. 3A–3B partially connected to share certain components.

The productivity of the present invention can be enhanced by having two rack assemblies share a single light source 16 as illustrated in FIG. 4 which depicts a 240-vial instrument based on joining two of the 120-vial assemblies that are shown in FIGS. 3A–3B. Each of the 120-vial racks 1' has its own emission detector components 22 and excitation/emission beam splitter 18. However, the two racks 1' obtain excitation energy from a single source 16 by use of a semi-transparent alignment mirror 117 as shown. One-half the energy of the source 16 is deflected to one of the two racks 1' and one-half is transmitted to the other. The use of a common source 16 and parallel detectors 22 for the two racks 1' allows the incorporation of supporting electronics which simultaneously sample the fluorescence from the samples contained within both racks 1'. The embodiment illustrated in FIG. 4 thus obtains doubled vial sampling throughput without the expense of multiple laser sources, thereby reducing the cost per sample analyzed.

Figure 5A:
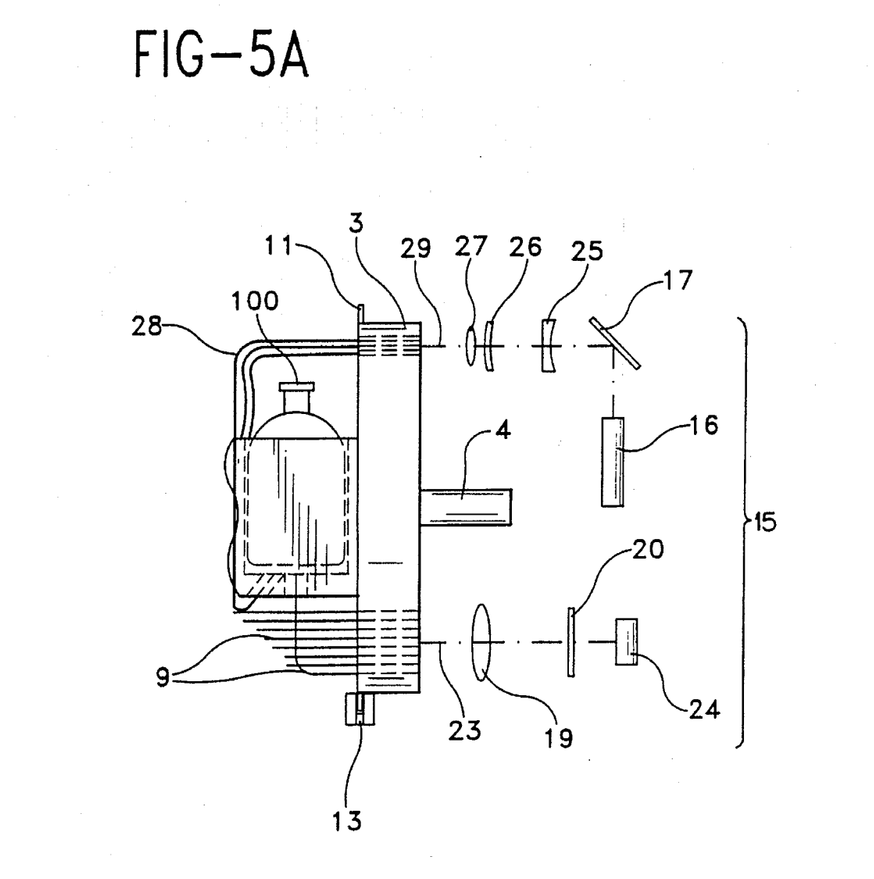
FIGS. 5A is a side elevation view illustrating details of an alternate detection systems used in the present invention.
Figure 5B:
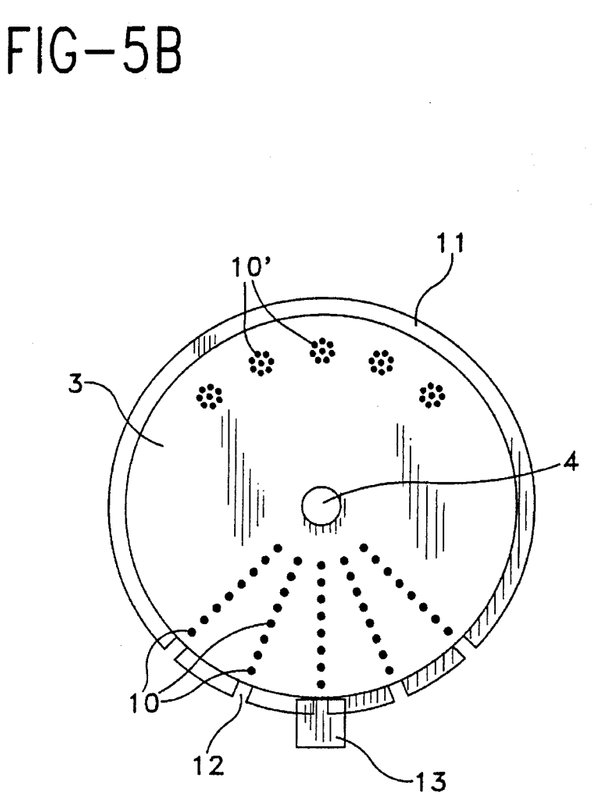
FIGS. 5B–5C are side elevation views similar to FIG. 1C illustrating alternate arrangements of optical coupling locations.
Figure 5C:
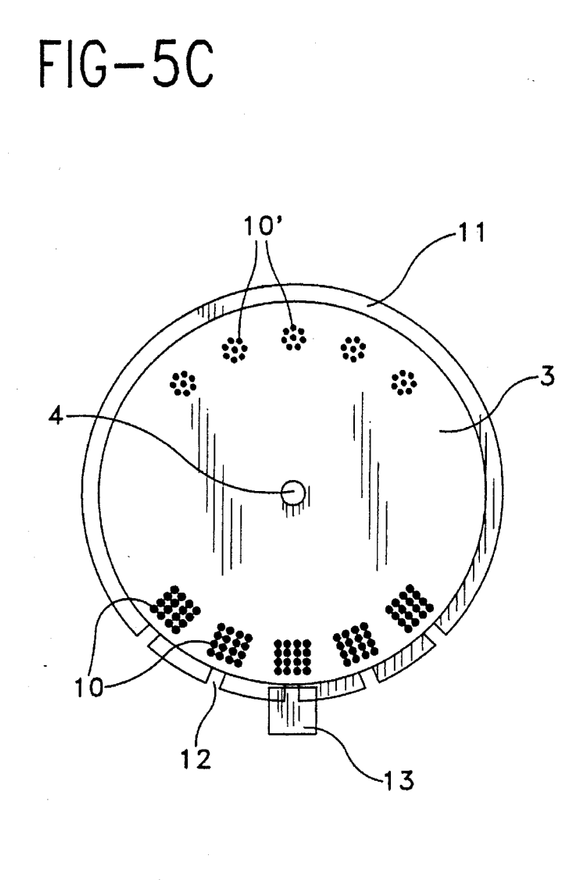

Referring now to FIGS. 5A–5B, an alternate embodiment of the present invention is illustrated in which separate optical fibers 28, 9 are used for excitation 28 and emission 29. FIG. 5A depicts a partially broken away elevation view of an instrument similar to those described above with reference to FIGS. 1A, 2 and 3B, except that the excitation/ detection system 15 differs, as explained herein. In this embodiment, three lenses 25, 26, 27 form a Galilean laser beam expander along the excitation beam axis 29; this beam simultaneously illuminates multiple vials 100 via a circular bundle of excitation fibers 28, the ends 10' of which may be arranged as seen in FIGS. 5B–5C or in any suitable pattern, in any reasonable subdivision, based upon the number of samples to be tested. The ends 10 of the emission fibers 9 from each of the simultaneously excited groups of vials 100 are preferably arranged into linear arrays by terminating each emission fiber 9 the sampling disk 3, as explained above. The arrays of fiber ends 10, 10' are most preferably centered on equi-angularly spaced radii of the sampling disk 3. As explained above, the apparatus is preferably indexed between optical coupling locations, defined by the array of fiber ends 10, 10' in this embodiment, using a series of notches 12 that cooperate with the fiducial 13 to produce an electrical signal indicating precise alignment.

Once aligned, a selected array of emission fiber ends 10 is optically coupled to a photodetector 24, seen in FIG. 5A, by an objective lens 19 centered on a central emission axis 23 of the array of the emission fiber ends 10. The photodetector 24 is either a linear photodiode array, avalanche photodiode array, or charge-coupled device (CCD). Alternatively, a fiber-optic face plate is used in some embodiments in place of the objective lens 19. In these embodiments, electronic readout of the elements of the linear photodetector array 20 then provides emission intensity measurements for the selected vials. As shown in FIG. 5C, the linear format of the arrays of emission fiber ends 10 that define the optical coupling locations is replaced in some embodiments with a square 4×4. In these embodiments, the linear photodetector array 24 is replaced with a sixteen channel photomultiplier tube.

Figure 6:
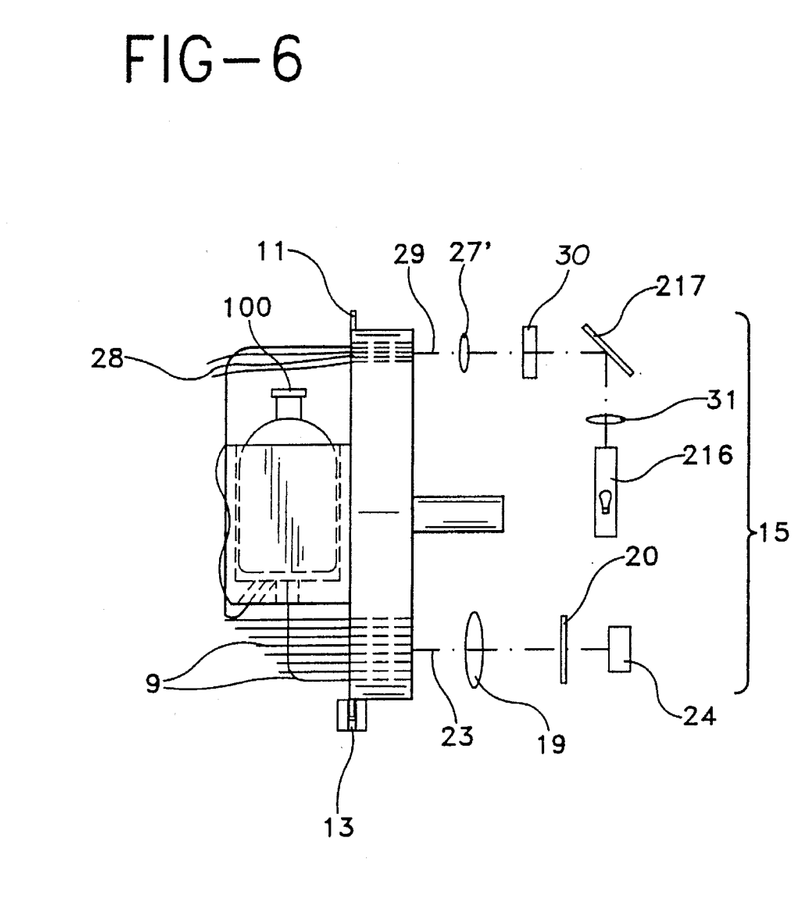
FIG. 6 illustrates details of another alternate embodiment an optical system for use in the present invention.

FIG. 6 shows another alternative embodiment of the apparatus of the present invention, in a view similar to FIG. 5A, in which the laser source 16 has been replaced by an arc lamp or filament lamp 216. The beam expander lenses 25, 26, 27 shown in FIG. 5A are eliminated, but due to the non-coherent nature of the arc lamp 216, a collimating lens 31, excitation filter 30 and focusing lens 27' are required. In this embodiment, the mirror 217 is most preferably a so-called "cold mirror" which directs only short-wavelength radiation toward the excitation fiber bundles 28. A cold mirror is a heat transmitting filter that permits the transmission of infrared wavelengths while reflecting visible light, such as those available from Driel Corporation, 250 Long Beach Blvd., P.O. Box 872, Stratford, Conn., USA 06497. In certain embodiments, the collimating lens 31 and the cold mirror 217 can also be combined and replaced with a single collimating cold mirror. The emission side of this detection system is similar to that described with reference to FIG. 5A.

Figure 7A:
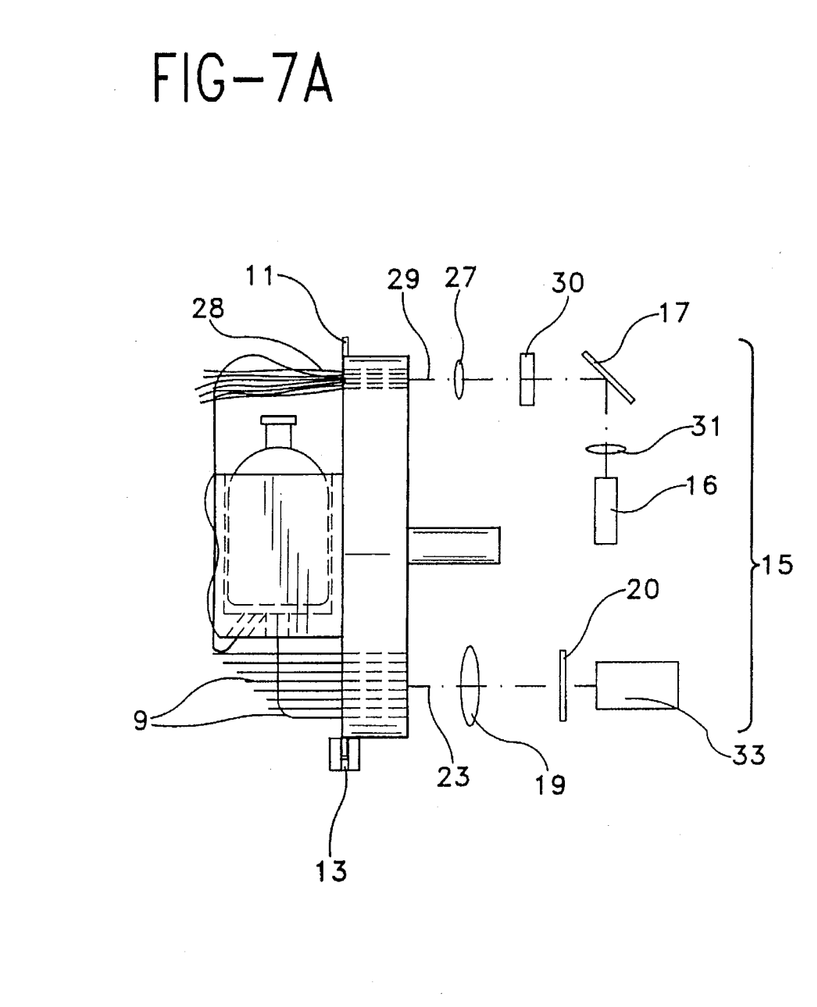
FIGS. 7A–7B illustrate details of still another alternate embodiment of the rack apparatus and optical system used in the present invention.
Figure 7B:
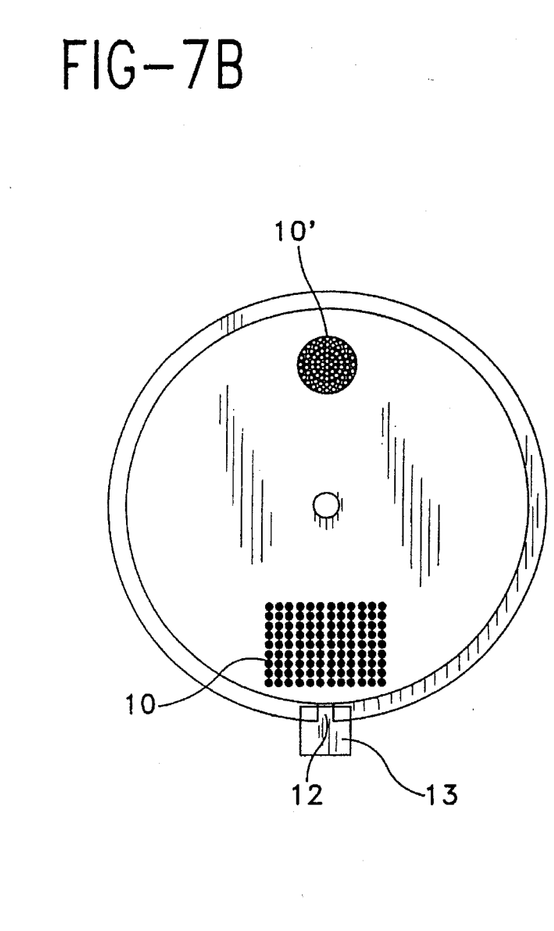

FIGS. 7A–7B illustrate an embodiment of the present invention that allows for the highest sampling throughput, although it also requires the greatest optical source power. In this embodiment, there is one registered rack position, a single bundle of excitation fiber ends 10', and one array of emission fiber ends 10. The photodetector 33 is most preferably a two-dimensional charge-coupled device (CCD), silicon-intensified target (SIT) detector or other high-sensitivity imaging detector. Also in this embodiment, the objective lens 19 can be replaced with a fiber-optic face plate, as described above with reference to FIG. 5A.

Figure 8:
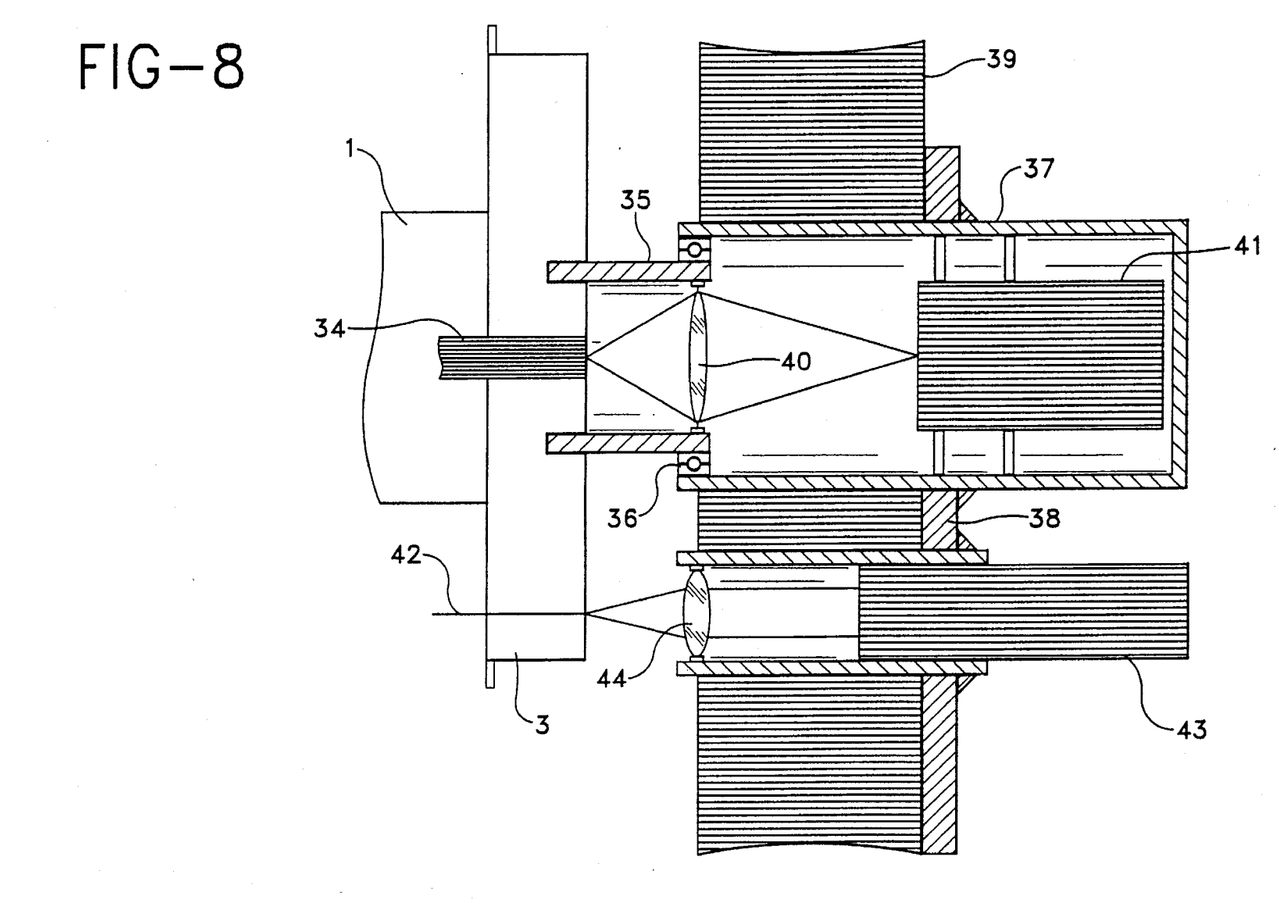
FIG. 8 is a partial, front elevation cross-sectional view of a light source and photodetector used in certain embodiments of the apparatus of the present invention.

A further modification of an apparatus according to the present invention is illustrated by the partial, cross-sectional side view of FIG. 8. In this embodiment, the emission fibers 34 are grouped together in an array located along the center axis of the circular sampling disk 3 of the rack 1. The rack 1 and disk 3 are connected to a supporting structure 38 via a rotatable coupling 35 that rides on a bearing 36 disposed within a housing 37, as shown. Emission light reemerging from the fiber bundle 34 is focussed on a photodetector 41 by an optical lens 40. In this embodiment, the excitation fibers 42 are preferably illuminated by a light source 43 using a second optical lens system 44. In a most preferred embodiment, a laser is used as the excitation light source 43. It should also be noted that the lens systems 40,44 are preferably constructed and adapted to act as insulating walls in order not to impair the thermal insulation 39 that insulates the structure 38 to retain heat in the area of the rack 1.

In this embodiment, the emission fiber bundle 34 can have an irregular statistical distribution of individual fibers and is still capable of monitoring individual sample vials 100. The photodetector 41 is most preferably a photomultiplier, and thus electromagnetic energy reemerging from each individual fiber in the emission bundle 34 always reaches the photodetector 41, independent of the particular sampling disk's angular position. However, the emission fiber bundle 34 may also be arranged in a regular 2-dimensional array comprising rows and columns, as shown for example in FIG.

7B. In this case, the photodetector 41 is most preferably an electronic camera. It is advantageous, however, to concentrate all excitation fibers into one irregular bundle 34. Therefore, as in the embodiment illustrated in FIGS. 7A–7B, the rack 1 most preferably has only one position for reading all sample vials. The embodiment shown in FIG. 8 provides an excellent optical shielding between the bundle of excitation fibers 42 and the emission fibers 34. This is due to the cylinder 35 surrounding the emission path that also forms part of the structure that acts as the pivot shaft for the rack 1. With regard to modifications, it is advantageous if the optical lens system 44 comprises a cylindrical lens to generate a slit-shaped fiber illumination beam with the slit axis oriented radially on the circular sampling disk 3. Using a slit-shaped fiber illumination beam results in a significant reduction of the mechanical precision requirements. This also results in an excellent long-time stability of the instrument.

One modification applicable to any of the embodiments of the apparatus of the present invention discussed above is the replacement of the stepper motor 5 with an ordinary electrical motor. In this case, the rack 1 and the circular sampling disk 3 rotate back and forth continuously. Whenever an excitation fiber crosses the focussed laser beam, light reemerges from the corresponding emission fiber. Consequently, the output signal generated by the photodetector consists of a series of pulses, and the pulse amplitudes contain information indicative of bacteriological activity. This multi-pulse signal is stored and analyzed by a computer.

An additional feature of preferred embodiments of apparatus made according to the present invention is described in FIGS. 9A–9B and 10A–10B. In this embodiment, a mechanism is provided that allows interchangeable rack subassemblies 101 holding a plurality of vials 100 to be easily mounted and dismounted. These embodiments of the present invention therefore can use a relatively small number of vials 100 per interchangeable rack subassembly 101 and make use of multiple racks 101 maintained in an external incubator (not illustrated). Each rack subassembly 101 is placed in the apparatus by an operator at appropriate times, and each of the vials 100 is spectrophotometrically tested for bacteria growth or otherwise exposed to electromagnetic radiation, as described above. The rack subassembly 101 is then replaced in the external incubator.

Figure 9A:
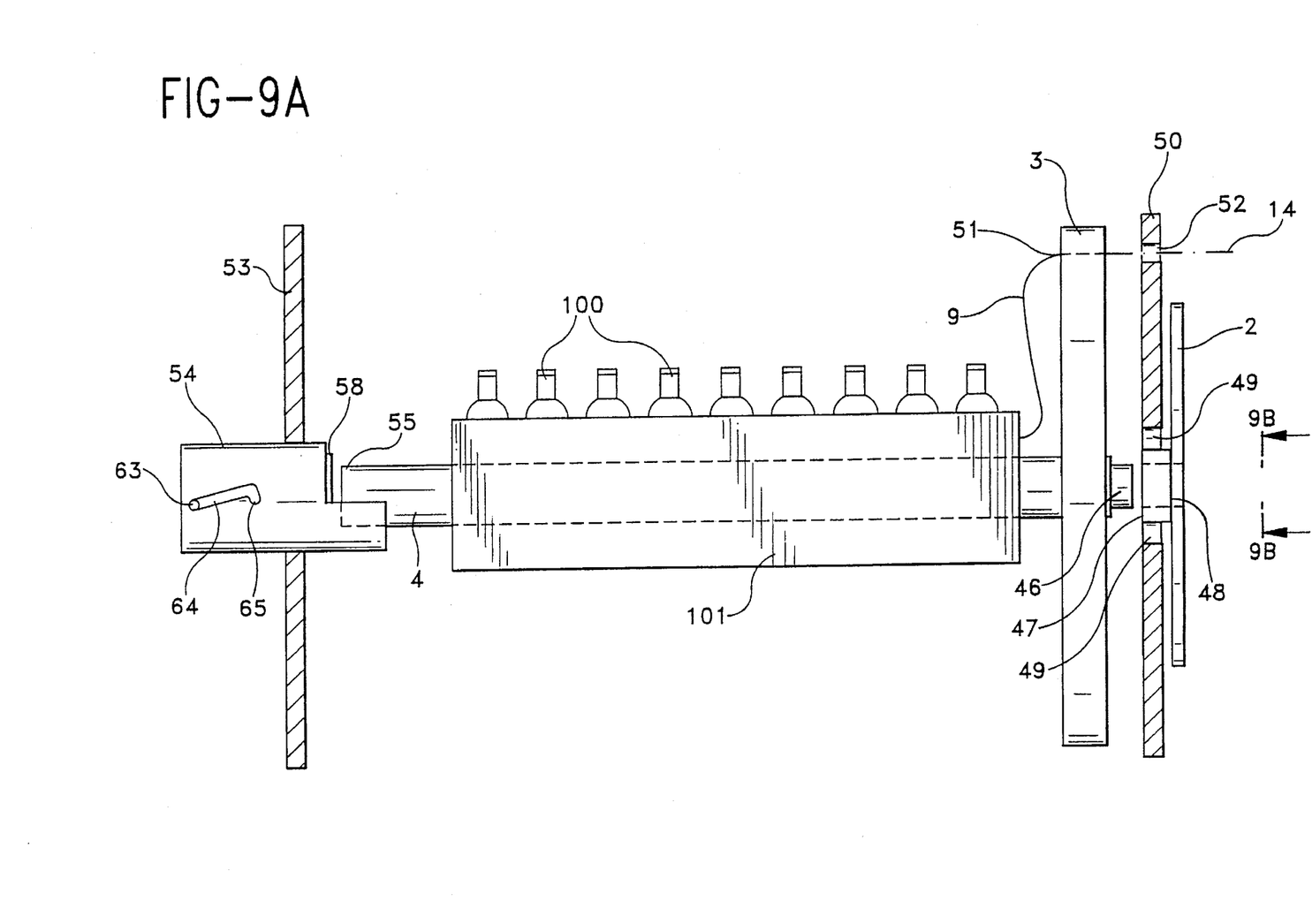
FIGS. 9A–9B depict another alternate embodiment of the rack apparatus of the present invention.
Figure 9B:
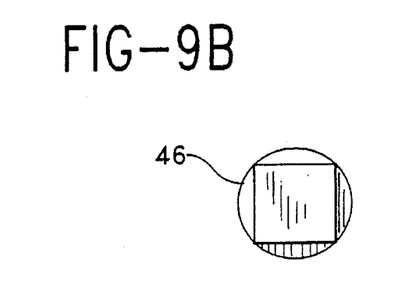

Further details of this embodiment are illustrated in FIGS. 9A–9B. The rack subassembly 101 has a pivot shaft 4 and contains a set of emission/excitation fibers 9 optically linked to an array of mounting holes 51 on the sampling disk 3. The anterior end 46 of the pivot shaft 4 is preferably formed into a square cross-section, as shown in FIG. 9B, and inserted into a matching square female socket 47 centered in hub 48 of the drive pulley 2. The drive pulley hub 48 rotates within a bearing 49, which is fixed in the incubator wall 50. For purposes of illustration, the remainder of the drive system is not shown. Spectrophotometric sampling of an individual optical fiber 9 aligned with the optical axis 14 is accomplished through an aperture 52 in the anterior incubator wall 50.

Figure 10A:
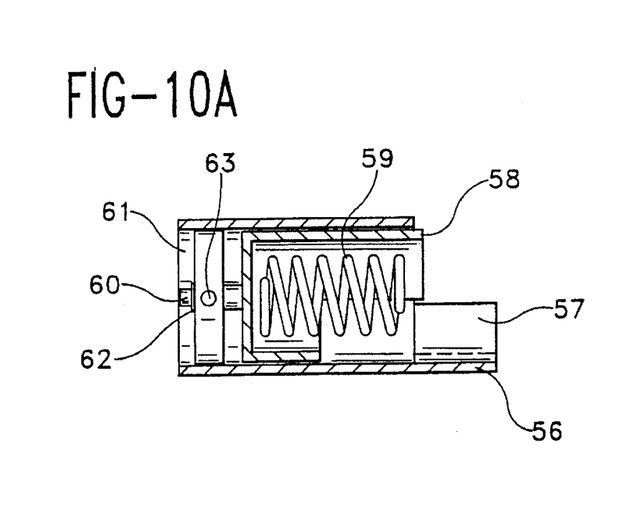
FIGS. 10A–10B illustrate further details of the rack apparatus depicted in FIGS. 9A–9B.
Figure 10B:
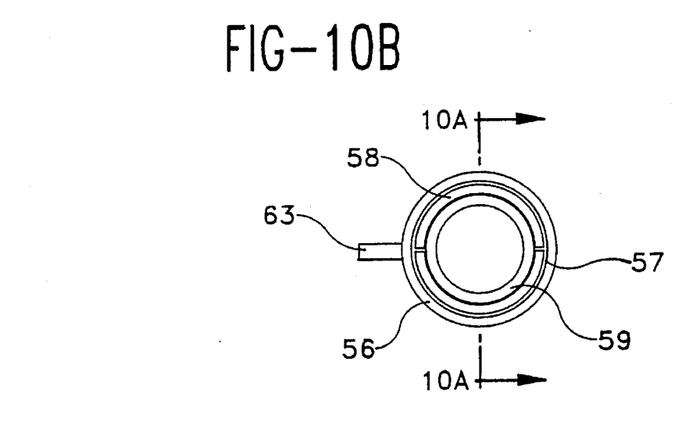

The posterior incubator wall 53 serves as fixed mounting for a bolt-action receiver 54 that supports the posterior end 55 of the pivot shaft 4. In a preferred embodiment, the receiver housing 56 is a hollow cylinder having a section removed from its anterior end in order to allow placement of the pivot shaft 4 within the open end. As seen in the side elevation view of FIG. 10B, the pivot shaft 4 rests on a semi-cylindrical supporting bearing 57 fixed inside the open end of the receiver 56. A hollow cylindrical bolt 58 nests inside the housing 56 and slides freely on the extended axis of the pivot shaft 4. When the bolt 58 is located in the retracted position as shown in FIGS. 9A and 10A, the pivot shaft 4 may be withdrawn and lifted out of the bolt-action receiver 54. This enables the entire rack subassembly 101 to be removed and placed in an external incubator or otherwise removed to a remote location.

When a rack subassembly 101 containing samples to be tested is put in place, the bolt 58 is placed in an extended position and captures the posterior end 55 of the pivot shaft 4, thereby preventing its removal. The compression spring 59, illustrated in FIG. 10A, is centered in the hollow bolt 58 and forces the pivot shaft 4 to the limit of its anterior travel in the socket 47 of the drive pulley hub 48. This mechanism controls the distance from the end of the optical fiber 9 to the aperture 52. Projecting from the solid rear wall of the bolt 58 is the actuator shaft 60, on which the actuator ring 61 rotates freely, and is retained by snap ring 62. The actuator handle 63 projects from the actuator ring 61 through the inclined slot 64 in the housing 56. By moving the actuator handle 63 in the slot 64, the bolt 58 may be extended or retracted; the short vertical detent slot 65 allows the bolt 58 to be locked in the extended position.

In addition to the various embodiments of the apparatus of the present invention described above, the present invention also provides methods for transmitting electromagnetic radiation to sample vials and receiving electromagnetic radiation from the sample vials. In order to practice the methods of the present invention, a plurality of sample vials are retained in a rack wherein one or more optical guides are coupled to each one of the plurality of sample vials and to the rack at one or more optical coupling locations. Next, an excitation/detection system, as described above, is provided for transmitting and receiving electromagnetic radiation between the excitation/detection system and the optical guides. The optical locations are aligned with the axis of the excitation/detection system. Finally, agitation of the sample vials is accomplished by a mechanical drive system, which also indexes the optical guides and aligns them with the axis of the excitation/detection system.

Those skilled in the art will realize that the various embodiments of the apparatus and methods disclosed herein are not limited to bacterial detection systems employing fluorescent sensors. In particular, the principles and concepts of the invention can be readily applied to chromophoric and absorptive sensors, to detection systems based on scattered photon migration, and to other optical sensor types that detect radiation at ultraviolet (UV), visible (VIS) or infrared (IR) wavelengths. In this regard, the present invention can be utilized in any situation where the size and the large number of agitated samples make direct sample imaging impractical. In a most preferred embodiment, however, the present invention provides an optical method and apparatus for promoting and detecting bacterial growth in blood culture vials which is simple, non-invasive, and that can be economically scaled for commercially-sized instruments. This design is potentially more reliable than designs having mechanical vial or detector transport systems because no electrical cables or fiber-optic cables cross the mechanical interface between the movable rack and fixed excitation/detection system. This design allows a single high-performance spectrophotometric detector to be economically shared among many culture vials; this enables the required measurements to be made with much better sensitivity, stability and dynamic range than can be achieved economically with detector components of low enough cost to be replicated at every vial position in a large instrument.

Thus, while the preferred embodiments of the present invention have been described so as to enable one skilled in the art to practice the apparatus and methods of the present invention, it is to be understood that variations and modifications may be employed without departing from the concept and intent of the present invention as defined in the following claims. The preceding description is intended to be exemplary and should not be used to limit the scope of the invention. The scope of the invention should therefore be determined only by reference to the following claims.

What is claimed is:

1. Apparatus for transmitting electromagnetic radiation to a plurality of sample vials and receiving electromagnetic radiation from the plurality of sample vials to detect bacterial growth within each vial, said apparatus comprising:

a rack having a pivot shaft for retaining a plurality of sample vials, each vial containing a chemical sensor that detects bacterial growth and emits a fluorescence intensity based upon detected bacterial growth when excited by electromagnetic radiation;

receiving means for receiving and supporting said pivot shaft, said receiving means having a retracted position wherein said rack and said pivot shaft can be removed from said receiving means and an extended position wherein said rack and said pivot shaft are captured by said receiving means;

an optical guide coupled at one end to one of said plurality of sample vials and coupled at the other end to said rack at an optical coupling location; and an excitation/detection system for transmitting and receiving electromagnetic radiation between said excitation/detection system and said chemical sensor within said one of said plurality of sample vials along said optical guide, when said excitation/detection system is aligned with said optical location, wherein electromagnetic radiation is transmitted from said excitation/detection system through said optical location and said optical guide to said chemical sensor in said one of said plurality of sample vials and electromagnetic radiation corresponding to the fluorescence intensity emitted from said chemical sensor in said one of said plurality of sample vials is transmitted back through said optical guide and said optical location to said excitation/detection system, so that bacterial growth within said one of said plurality of sample vials is detected based upon the fluorescence intensity emitted from said chemical sensor.

2. The apparatus of claim 1, wherein a single optical guide is connected to each sample vial, and each of the single optical guides is connected to the rack at said optical location.

3. The apparatus of claim 2, wherein the excitation/detection system defines a single optical axis for transmitting and receiving electromagnetic radiation, and said optical coupling location is aligned with the optical axis.

4. The apparatus of claim 3, wherein the excitation/detection system comprises an emission mirror having an aperture through which electromagnetic radiation is transmitted, whereby the emission mirror reflects electromagnetic radiation received from the optical location to a detector.

5. The apparatus of claim 1, wherein the optical guide comprises:

a first portion for receiving electromagnetic radiation at said optical location and for transmitting the electromagnetic radiation to said chemical sensor; and a second portion for collecting electromagnetic radiation from said chemical sensor and transmitting the collected electromagnetic radiation to said optical location.

6. The apparatus of claim 5, wherein the first portion comprises an excitation fiber and the second portion comprises an emission fiber.

7. The apparatus of claim 6, wherein said optical location comprises a plurality of excitation fiber ends.

8. The apparatus of claim 5, wherein:

said rack includes a central longitudinal axis;

said first portion of said optical guide is coupled to said rack at said optical coupling location that is aligned with the central longitudinal axis of said rack; and said apparatus further comprises a source of electromagnetic radiation aligned with the central longitudinal axis of said rack.

9. The apparatus of claim 1, further comprising a motorized agitation system that indexes the rack into alignment with said optical coupling location and agitates samples held in the sample vials.

10. The apparatus of claim 1, wherein the excitation/detection system comprises a first source of electromagnetic radiation.

11. The apparatus of claim 10, further comprising:

a second rack for holding a second plurality of sample vials, each vial containing a chemical sensor that detects bacterial growth and emits a fluorescence intensity based upon detected bacterial growth when excited by electromagnetic radiation, and having a second optical guide coupled at one end to one of said second plurality of sample vials and coupled at the other end to said second rack at a second optical coupling location; and a second excitation/detection system for transmitting and receiving electromagnetic radiation between said second excitation/detection system and said chemical sensor within said one of said second plurality of sample vials along said optical guide, when said second excitation/detection system is aligned with said optical location, to detect bacterial growth within said one of said second plurality of sample vials based upon the fluorescence intensity emitted from said chemical sensor.

12. A method for transmitting electromagnetic radiation to a plurality of sample vials and receiving electromagnetic radiation from the plurality of sample vials to detect bacterial growth within each vial, said method comprising the steps of:

providing a plurality of sample vials, each vial containing a chemical sensor that detects bacterial growth and emits a fluorescence intensity based upon detected bacterial growth when excited by electromagnetic radiation;

retaining the plurality of sample vials in a rack having a pivot shaft;

supporting said pivot shaft in a bolt-action receiver, wherein said rack and said pivot shaft can be removed from said bolt-action receiver, when said bolt-action receiver is in a retracted position, and said rack and said pivot shaft are captured by said bolt-action receiver, when said bolt-action receiver is in an extended position;

coupling an optical guide to each one of the plurality of sample vials and to the rack at an optical coupling location;

transmitting and receiving electromagnetic radiation between an excitation/detection system and the optical guide; and aligning the optical location with the excitation/detection system, whereby electromagnetic radiation is transmitted from the excitation/detection system through the optical location and the optical guide to a chemical sensor in one of the plurality of sample vials and electromagnetic radiation corresponding to the fluorescence intensity emitted from the chemical sensor in said one of the plurality of sample vials is transmitted back through the optical guide and the optical location to the excitation/detection system, so that bacterial growth within said one of the plurality of sample vials is detected based upon the fluorescence intensity emitted from the chemical sensor.

13. The method of claim 12, further comprising the step of moving said rack and said optical guide.

14. The method of claim 12, further comprising the steps of:

receiving electromagnetic radiation at the optical location using a first portion of the optical guide;

transmitting electromagnetic radiation to the chemical sensor;

collecting electromagnetic radiation from the chemical sensor using a second portion of the optical guide; and transmitting the collected electromagnetic radiation to the optical location.

15. The method of claim 12, further comprising the step of indexing the rack into alignment with said optical coupling location; and agitating samples held in the sample vials.

16. The method of claim 14, further comprising the step of transmitting electromagnetic radiation to a first rack and a second rack, the first and second racks retaining a first plurality and a second plurality of sample vials, respectively.

* * * * *